(12) United States Patent
Graves et al.

(10) Patent No.: US 8,277,452 B2
(45) Date of Patent: Oct. 2, 2012

(54) BONE RESECTION DEVICE

(75) Inventors: William Graves, Cheltenham (AU); David Harry Sonnabend, Rose Bay (AU); William Robert Walsh, Maroubra (AU)

(73) Assignee: Depuy International Limited (GB)

( * ) Notice: Subject to any disclaimer, the term of this patent is extended or adjusted under 35 U.S.C. 154(b) by 1295 days.

(21) Appl. No.: 10/564,717

(22) PCT Filed: Dec. 11, 2003

(86) PCT No.: PCT/GB03/05437
§ 371 (c)(1),
(2), (4) Date: Dec. 8, 2006

(87) PCT Pub. No.: WO2004/052216
PCT Pub. Date: Jun. 24, 2004

(65) Prior Publication Data
US 2007/0276391 A1    Nov. 29, 2007

(30) Foreign Application Priority Data
Dec. 12, 2002 (GB) .................................. 0228964.3

(51) Int. Cl.
*A61B 17/00* (2006.01)
(52) U.S. Cl. ............................................ 606/83; 606/79
(58) Field of Classification Search ............... 606/79–89
See application file for complete search history.

(56) References Cited

U.S. PATENT DOCUMENTS

| | | | |
|---|---|---|---|
| 3,702,611 A | 11/1972 | Fishbein | |
| 4,011,025 A | 3/1977 | Kress | |
| 4,621,637 A | 11/1986 | Fishbein | |
| 4,943,291 A * | 7/1990 | Tanguy | 606/64 |
| 4,992,010 A * | 2/1991 | Fischer | 408/159 |
| 5,242,461 A * | 9/1993 | Kortenbach et al. | 606/159 |
| 5,445,639 A | 8/1995 | Kuslich | |
| 5,853,054 A * | 12/1998 | McGarian et al. | 175/267 |
| 5,913,867 A | 6/1999 | Dion | |
| 6,383,188 B2 * | 5/2002 | Kuslich et al. | 606/80 |
| 6,884,246 B1 * | 4/2005 | Sonnabend et al. | 606/80 |
| 7,429,264 B2 * | 9/2008 | Melkent et al. | 606/159 |
| 2001/0034526 A1 * | 10/2001 | Kuslich et al. | 606/80 |
| 2005/0222571 A1 * | 10/2005 | Ryan | 606/80 |
| 2006/0064100 A1 * | 3/2006 | Bertagnoli et al. | 606/79 |

FOREIGN PATENT DOCUMENTS

| | | | |
|---|---|---|---|
| WO | WO 01/34040 A1 * | 10/2000 | |
| WO | WO 0134040 A1 | 5/2001 | |
| WO | WO 0160268 A1 | 8/2001 | |

OTHER PUBLICATIONS

EPO Examination Report in a case related to the above US appln dated May 20, 2009 (4 pages).

* cited by examiner

*Primary Examiner* — Thomas Barrett
*Assistant Examiner* — Matthew Lawson

(57) ABSTRACT

A bone resection device for use in resection of bone during joint replacement surgery includes a handle, an elongate shaft rotatably mounted to the handle, a cutting tool housing attached to the shaft at or towards the distal end of the shaft, at least one cutting tool fastened to the housing, and a pivot control member configured to be at least partially disposed about the elongate shaft, the pivot control member being attached at or toward the distal end of the pivot control member to the at least one cutting tool, the distal end of the pivot control member and the distal end of the shaft being configured to be axially displaceable with respect to one another a predetermined distance, during operation of the device.

24 Claims, 4 Drawing Sheets

BONE RESECTION DEVICE

The present invention relates to a surgical instrument for the controlled removal of bone during joint replacement surgery.

Such instruments are commonly referred to as reamers or millers. Conventionally available instruments generate a resected surface which is of fixed shape (for example circular), dependent upon the particular instrument used. However, sometimes it is necessary to cut more complex shapes, and attempts have been made to provide instrumentation capable of this.

WO-01/34040 discloses a bone resection device which comprises a rotatable shaft having two blades pivotally mounted on it so that they can rotate with the shaft. A blade positioning mechanism is mounted on the device to alter the orientation of the cutting edges of the blades relative to the shaft so that the shape of the resected surface is determined in part by the blade positioning mechanism.

The blade positioning mechanism comprises a cam surface and a cam follower assembly which controls the pivotal position of the blades according to movement of the cam follower over the cam surface during rotation of the shaft. The cam surface and cam follower are located at the distal end of the shaft where the blades are mounted on the shaft. This makes the disclosed device bulky at its distal end.

The present invention provides a bone resection device which includes device for controlling the pivotal position of the cutting tool, the control device extending along the shaft and being movable relative to the shaft along the axis defined by the shaft, and engaging the cutting tool at or about its distal end.

Accordingly, in a first aspect, an example of the invention provides a bone resection device for use in resection of bone during joint replacement surgery, the device comprising:
 a handle;
 an elongate shaft rotatably mounted to the handle, the shaft having a shaft axis, a proximal end and a distal end;
 a cutting tool housing attached to the shaft at or towards the distal end of the shaft; at least one cutting tool fastened to the housing, the at least one cutting tool configured to be movable between a retracted position and an extended position;
 a pivot control member having a proximal end and a distal end, the pivot control member configured to be at least partially disposed about the elongate shaft, the pivot control member being attached at or toward the distal end of the pivot control member to the at least one cutting tool, the distal end of the pivot control member and the distal end of the shaft being configured to be axially displaceable with respect to one another a predetermined distance, during operation of the device; and
 a cam follower, and wherein one of the pivot control member and the shaft comprises a cam surface configured to accept the cam follower, the cam surface extending in a plane generally perpendicular to the shaft axis, and wherein the cam follower is fixed relative to the handle, and of the cam surface is fixed relative to the pivot control member.

The bone resection device of the invention has the advantage that the device for controlling the position of the cutting tool is movable relative to the shaft, along the axis defined by the shaft, so that the orientation of the cutting tool can be determined according to components (for example by means of a cam surface and cam follower) spaced apart from the housing at the end of the shaft, for example at or around the proximal end of the shaft. The ability of the control device to move axially relative to the shaft allows the configuration of the cutting tool to be controlled as desired. In this way, the connection between the control device and the cutting tool can be kept simple, allowing it to be kept small.

The control device can have the form of a sleeve within which the shaft can rotate. The sleeve can have side walls which are open, at least partially. The control device will generally rotate with the housing and the shaft.

Preferably, there are at least two cutting tools in the housing. Preferably, the or each cutting tool is fastened to the housing pivotally so that it can be moved pivotally between retracted and extended positions. It will often be preferred for two cutting tools to be fastened to the housing in opposed manner such that when one of the cutting tools is caused to pivot in one direction the other cutting tool is caused to pivot to the same degree in the opposite direction. When the connection between the pivot control device and the cutting tools is provided by elongate cam tracks on the cutting tools and a cam follower on the control device, the relative motion between the cutting tools can be controlled by appropriate design of the shape of the cam tracks. When it is desired for the cutting tools to move in equal and opposite amounts, the cam tracks can be approximately the same shape. However, it can be preferred for some applications for movement of the cutting tools to be other than equal and opposite. In this case, this can be arranged by use of appropriately shaped cam tracks. For example, the cam track for one of the cutting tools can be inclined to the axis of the device and that cutting tool will then move between extended and retracted positions. The cam track on the other cutting tool can extend parallel to the axis of the device, and as a result, that cutting tool will not move pivotally.

The cutting tools can be arranged to slide in the housing instead of pivoting. Sliding movement of the cutting tools can be controlled by means of a cam track and cam follower arrangement, for example comprising a slot which defines a cam track, and a pin which slides in the track. For example, each blade might have a slot formed in it, and the slide control device can include a pin which reciprocates along the axis of the shaft, causing the cutting tools to reciprocate slidingly, in a direction which might be perpendicular to the axis of the shaft. Alternatively, the slide control device can have a slot in it, and each of the cutting tools can have a pin which slides in the slot as the tools reciprocate slidingly.

The device of the invention will generally include a handle with a bore extending through it in which the shaft is mounted for rotation relative to the handle. The shaft can include a connector formation by which it can be connected to a drive unit for imparting rotational movement to the shaft. For example, the shaft can have a boss, especially with a non-circular (for example a hexagonal) cross-section for fitting into a hexagonal socket on a rotational drive unit. Alternatively, the shaft can have a socket with a non-circular bore, for receiving a correspondingly shaped boss on a drive unit.

Movement of the control device relative to the shaft can be controlled by means of a cam surface extending in a plane generally perpendicular to the axis defined by the shaft and a cam follower. One of the cam surface and the follower can be fixed relative to the handle, and the other can then be fixed relative to the control device. Relative rotational movement between the control device and the handle can then the follower to move over the cam surface, causing relative axial movement between the control device and the shaft.

Preferably, the cam surface is provided on the control device. For example, a groove can be formed in the control device, facing radially outwardly. The groove can receive a cam follower in the form of one or more pins, each of which is fixed to the inside of the housing.

The shape of the surface which is formed in a bone by the cutting tool(s) is determined by the axial movement of the control device as the shaft rotates. When the axial position of the control device is determined using a cam surface and associated cam follower, the shape of the resected bone surface can be determined by the shape of the cam surface. It will generally be preferred for the cam surface to have a symmetrical configuration about the axis defined by the shaft.

It can be preferred for some applications for the device of the invention to create a resected area on the bone surface which is non-circular. The reversible motion of the cutting tools as the shaft of the device rotates can cause the radial extent of the cutting surface to vary. In this way, the shape of the resected area on the bone surface can be made non-circular, for example oval, or ovoid (rounded ends and relatively straight sides).

Preferably, the device includes a locking mechanism to lock the shaft and the control device in a reference position, from which they are made to move axially relative to one another when the shaft is rotated. For example, when the axial movement of the control device is determined with reference to the handle, the locking mechanism can lock the shaft axially relative to the handle. Preferably, the locking mechanism can be adjusted to provide different reference positions of the shaft relative to the control device, especially relative to the handle.

A preferred locking mechanism comprises a lock ring which fits into a groove on the shaft so that the shaft passes through the lock ring and can rotate relative to the lock ring. However, the axially facing ends of the lock ring prevent relative axial movement between the shaft and the lock ring. The lock ring can engage the handle, for example using an external screw thread which engages an internally threaded bore in the handle. Movement of the lock ring relative to the handle, by means of the thread on the lock ring, causes the shaft to move axially relative to the handle. The locking mechanism can include a spacer (for example in the form of a spacer ring which has an open side to enable it to be slid over the shaft) which can fit between the lock ring and the end wall of the handle, to control the axial position of the shaft relative to the handle when the lock ring is screwed tightly into the handle. Preferably, the device includes a plurality of spacers with a range of widths, to define different reference positions for the shaft relative to the control device.

Preferably, the or each cutting tool is generally elongate in shape, with a cutting edge towards one end and the elongate cam track or reciprocating follower for engaging the control device at its opposite other end. It will generally be preferred for the cutting edge to face directly away from the end which engages the control device. The shape of the cutting edge will depend on factors such as the nature of the cutting action (for example as might be performed by a blade, a rasp, a reamer or a grater), and the desired shape of the resected surface. When the resected surface has the shape of a generally rounded recess, the cutting edges will preferably be rounded.

Preferably, the cutting tools are removable from the device, and the device includes at least one other interchangeable cutting tool. This can enable the device to be used to create bone resection surfaces with desired configurations by selection of an appropriate cutting tool. Examples of tools which can be incorporated into the device include blades, reamers, graters and rasps. The device can include any of the tools of these general kinds. It can include more than one blade (or other tool), the blades (or other tools) differing from one another in terms of the configuration of the resected surface they define, for example by virtue of having different shapes or sizes. The cutting tool can also differ in terms of the shape of an elongate cam track by which it engages the control device. If the cam surface is provided on a component of the device which can be removed, a replacement component can provide a cam surface which can be used to generate a different shape of resected bone surface.

Preferably, the device includes a protruding boss at its distal end which is aligned with the shaft and provided on the end which is remove from the shaft. The boss can be provided on the distal end of the housing. Preferably, the boss includes a journaled cap or sleeve which can engage the bone and remain stationary relative to the bone as the shaft and the housing rotate when the device of the invention is in use.

The device can include location means for controlling its location during use relative to the patient's tissue. The location means can rely on reference points provided on the patient's tissue or on the operating table.

The device can be powered or hand-operated, or both. The device can include a handle which can be arranged in line with the shaft or at an angle thereto.

The device of the invention can be used to prepare a patient's bone to receive a component of a prosthetic joint. Examples of bones which can be prepared in this way include the tibia during implantation of a knee joint, the glenoid during implantation of a shoulder joint, the talus during implantation of an ankle joint, and the acetabulum during implantation of a hip joint.

Embodiments of the present invention will now be described, by way of example only, with reference to the accompanying drawings, in which.

Figure 1:
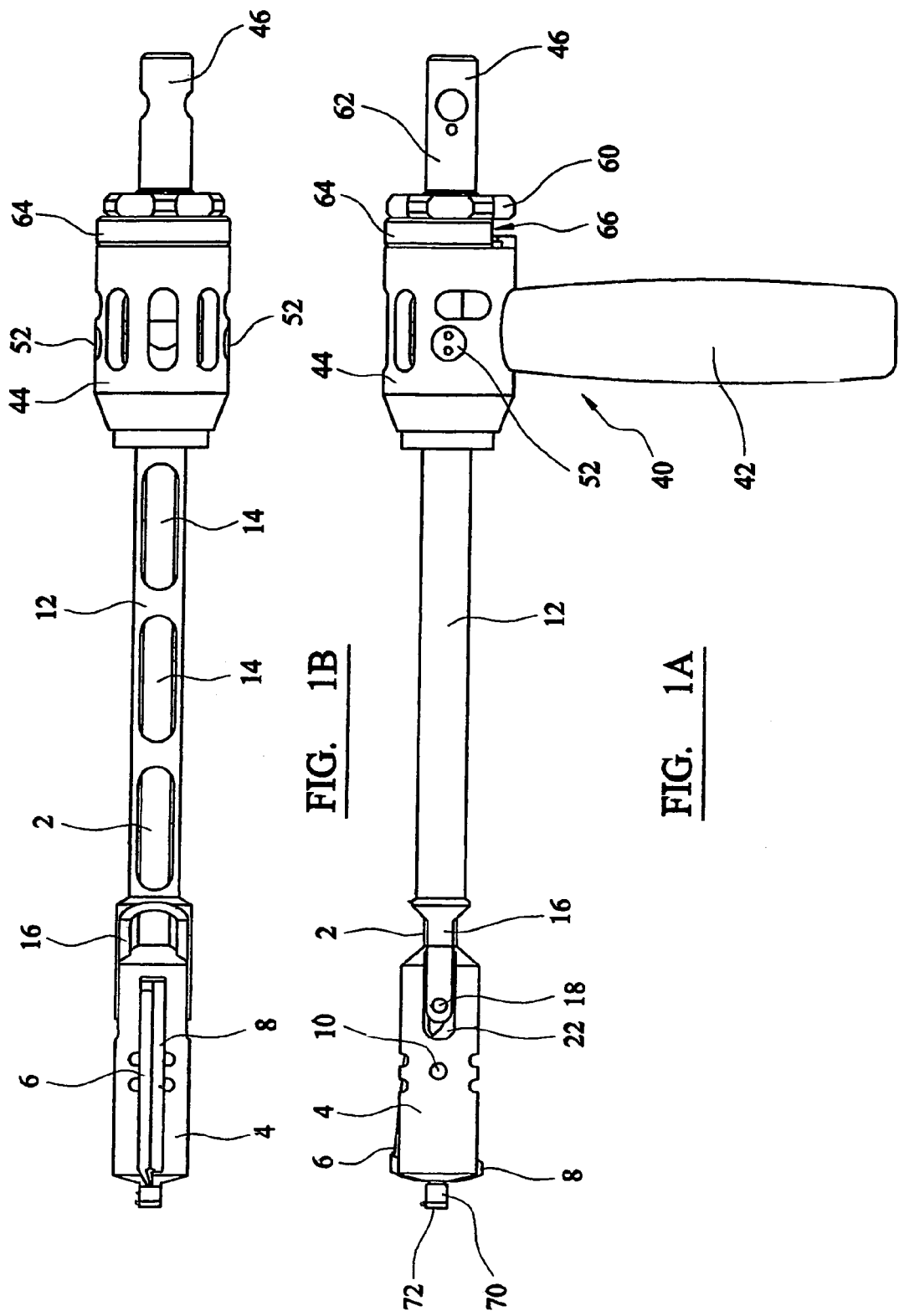
FIG. 1a is a side view of the device of the present invention.
FIG. 1b is a view from above of the device of the present invention.
Figure 2:
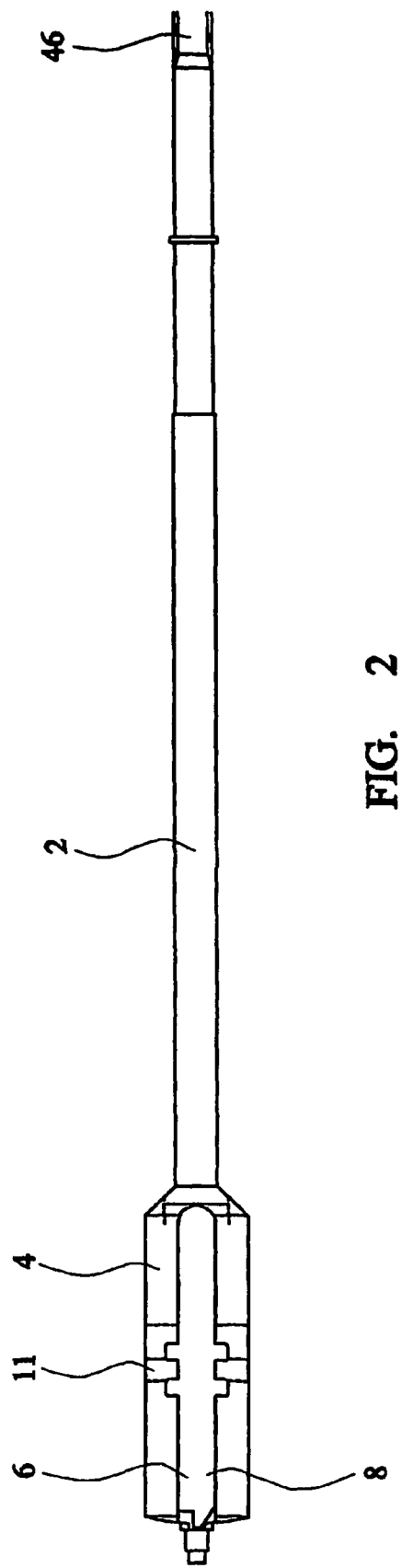
FIG. 2 is a view from above of the shaft component of the device shown in FIG. 1.

FIG. 1 shows a bone resection device for use in a resection of bone during joint replacement surgery. The device comprises an elongate shaft 2 which has a blade housing 4 at its distal end. The blade housing has two blades 6, 8 fastened to it, each of the blades being capable of pivotal movement between a retracted position and an extended position. Each blade extends further from the housing when in its extended position than when in its retracted position. As shown in FIG. 1A, the lower blade 8 is almost fully retracted within the housing. The upper blade 6 is partially extended from the housing. The blades pivot around a pivot pin 10 which is received within a through bore 11 in the housing. As can be seen in FIG. 2, the blade housing has an elongate slot in which the blades 6, 8 are housed and can slide.

The bone resection device of the invention includes a device 12 for controlling the pivotal positions of the blades 6, 8 relative to the housing 4. The pivot control device takes the form of a sleeve which has a hollow bore in which the shaft 2 is received. The sleeve has openings 14 in its side wall.

At its distal end, the pivot control device 12 has two parallel arms 16. A pin 18 extends between the arms 16, through aligned bores 20 in the arms.

Figure 4:
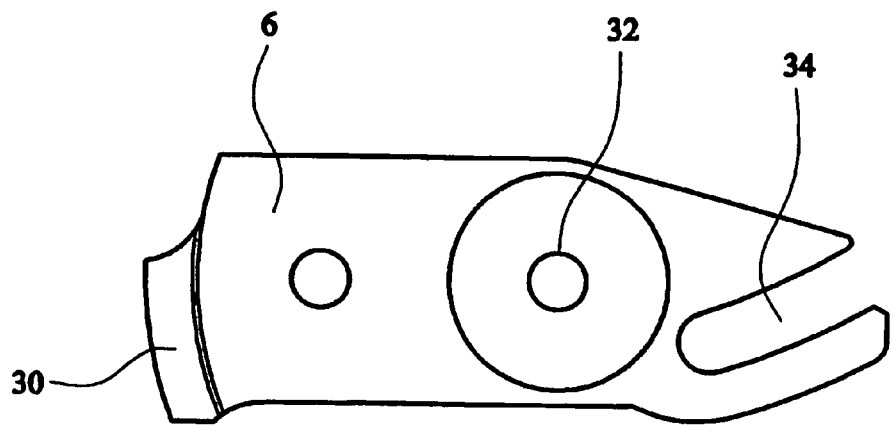
FIGS. 4 and 5 are views from above of cutting blades for use in the device shown in FIG. 1.
Figure 5:
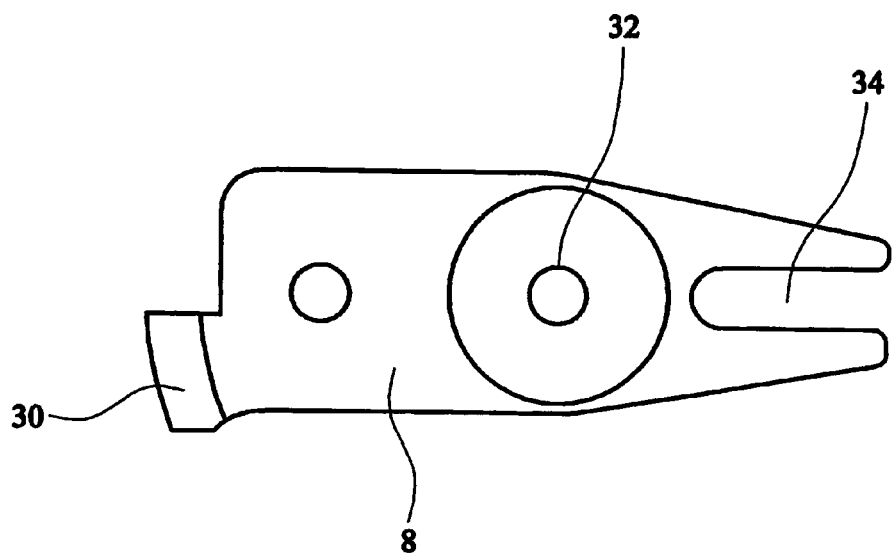

Blades 6, 8 for use in the device shown in FIG. 1 are shown in FIGS. 4 and 5 respectively, Each of the blades is formed from a sheet of a suitable material, generally metallic, especially a stainless steel as commonly used for surgical instruments. It can be preferred for some applications for a metal blade to be coated with a low friction polymer such as polytetrafluoroethylene. Each of the blades has a cutting edge 30 at one end. Each blade has a hole 32 extending through it to receive the pin 10 about which it pivots. At the end opposite to the cutting edge 30, each blade has a slot 34 formed in it. In the blade shown in FIG. 5, the slot is generally aligned with the axis of the blade. In the blade shown in FIG. 4, the slot is arranged at an angle to the axis, and is slightly curved.

Referring now to FIGS. 1a and 1b, the blades 6, 8 are located within the blade housing 4. The pivot control device 12 is arranged so that it slides on the shaft 2. The pin 18 which extends between the arms 16 of the pivot control device 12 extends through a slot 22 in the blade housing 4, and through the slots 34 in the blades 6, 8 within the housing. Axial movement of the pivot control device 12 relative to the shaft 2, the blade housing 4, and the blades 6, 8 causes the pin 18 to slide in the manner of a cam follower within the slots 34 in the blades 6, 8, the slots defining an elongate cam track. The straight slot in the blade 8 (see FIG. 5) means that movement of the pin 18 within the said slot does not give rise to any pivotal movement of the blade 8. In contrast, the arrangement of the slot 34 in the blade 6, inclined to the axis of the blade and slightly curved, causes the blade to move pivotally around the hole 32 as the pivot control device 12 and associated pin 18 moves relative to the shaft 2 and blade housing 4. The area of the bone around the axis of the device is covered effectively by the blade with the straight slot, even when the blade with the curved slot has moved outwardly to a significant degree to cover radially spaced regions of the bone.

The movements of the shaft 2 and the blade control device 12 during use of the device is controlled from the proximal end of the device. At this end, the device includes a handle 40 which includes a grip portion 42 and a guide portion 44. The guide portion has a bore extending through it. The shaft 2 extends through the guide portion 44 of the handle 40 so that it can be engaged at the shaft proximal end 46 by a drive unit, such as an electrically powered drive unit. This can engage the shaft using appropriate connectors, such as hexagonal boss fitting into a hexagonal socket. Rotational motion imparted to the shaft at the proximal end 46 is transmitted through the guide portion 44 of the handle 40 to the blade housing 4 and associated blades 6, 8.

Figure 3:
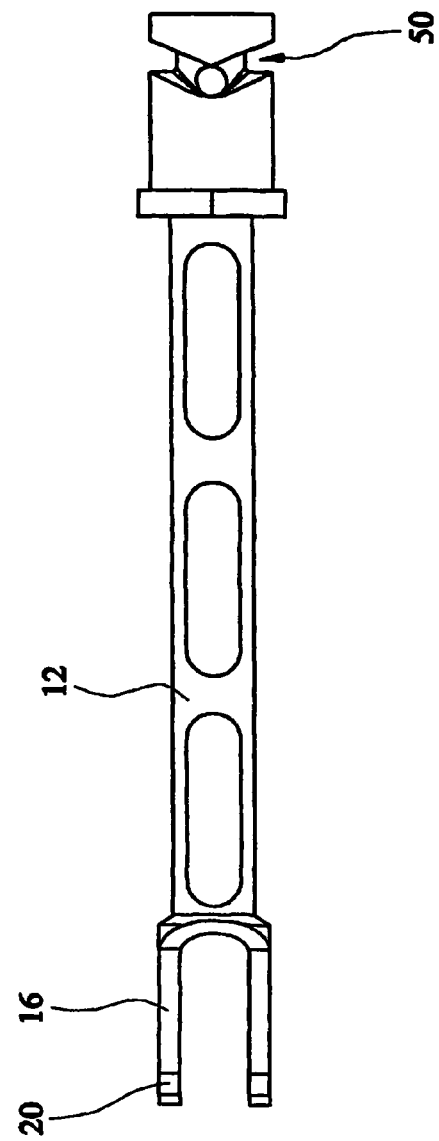
FIG. 3 is a view from above of the control device component of the device shown in FIG. 1.

The pivot control member 12 rotates relative to the handle 40 with the shaft 2. The pivot control member is made to move in a reciprocating fashion on the shaft 2. Movement of the pivot control member 12 is controlled by means of a cam track 50 on the pivot control member. The cam track is arranged generally on a plane which is perpendicular to the axis defined by the shaft 2, but is non-planar (as can be seen in FIG. 3). Two pins 52 protrude from the internal wall of the guide portion 44 of the handle 40 and extend into the cam track 50 on the pivot control member 12. One of the pins 52 can be seen in FIG. 1A. The other pin is diametrically opposite to the pin which is shown. Accordingly, as rotational motion is imparted to the shaft 2 (as described above), the pivot control member is made to rotate at the same time. Movement of the guide pins 52 within the cam track 50 causes the pivot control member then to move in a reciprocating fashion axially along the shaft 2. As described above, this causes the blade 6 within the blade housing 4 to move in and out of the blade housing, between the extended and retracted positions.

The relative axial positions of the shaft and the pivot control member, from which the pivot control member is made to move by means of the cam track 50 and following pins 52, is controlled by means of a threaded lock ring 60 acting against an end plug 62 on the shaft 2. The lock ring 60 is threaded at one end, and is received in a threaded bore in the guide portion 44 of the handle 40. A spacer ring 64 (which is open at one side 66 to enable it to be slid over the shaft) can be located between the lock ring 60 and the guide portion 44 of the housing. The lock ring 60 can then be screwed up tight into the guide portion of the handle, against the spacer ring 64. The lock ring then defines the axial position of the shaft 2 relative to the guide portion of the handle, and thereby also to the pivot control device 12. In this way, the location of the blades in the blade housing in their retracted and extended positions are defined. Different spacer rings 64 can be used to define different extended and retracted positions for the blades.

The device of the invention includes a protruding boss 70 at the distal end of the blade housing 4. The boss includes a journaled cap 72. The boss can be received within a pre-drilled hole in a patient's bone to define the working position of the device of the invention.

The device of the invention can be used to form a non-circular recess in a patient's bone. The device shown in the drawings can be used to ream a patient's bone to form a curved recess. The recess, when viewed from above, will be non-circular by virtue of the fact that the blade 6 is made to move between extended and retracted positions as the blade housing 4 rotates with the shaft 2. The shape of the resulting recess will be generally oval or ovoid.

Figure 6A:
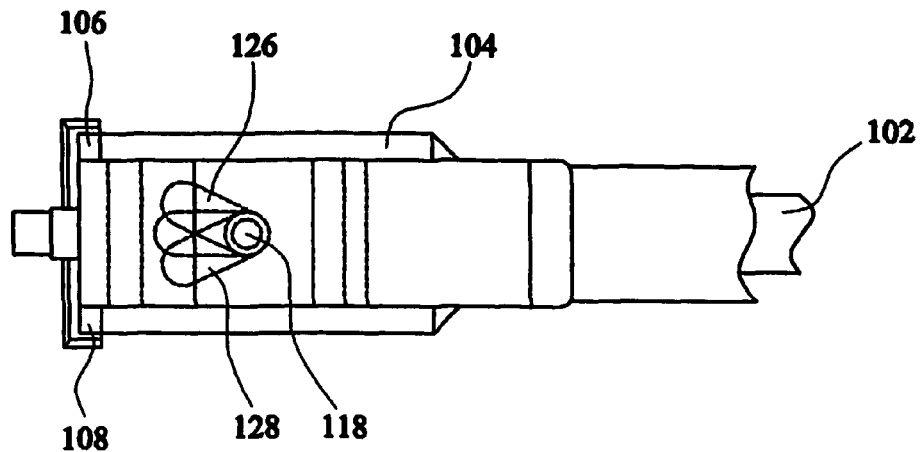
FIGS. 6a and 6b are side views, partially in section, showing a resection device in which cutting tools slide reversibly between retracted and extended positions.
Figure 6B:
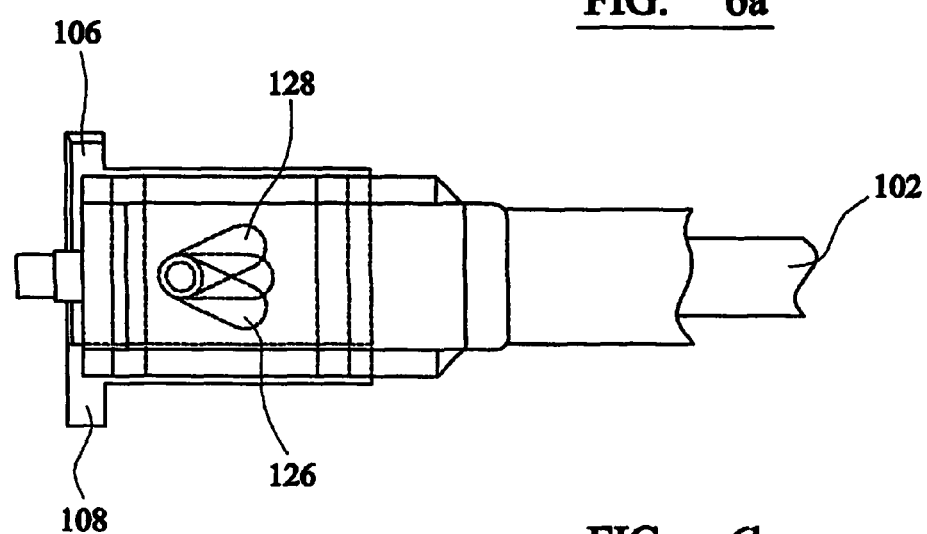

FIGS. 6a and 6b show the head portion of a bone resection device, which comprises an elongate shaft 102 with a blade housing 104 at its distal end. The blade housing has two blades 106, 108 fastened to it, each of the blades being capable of sliding movement between a retracted position (as shown in FIG. 6a) and an extended position (as shown in FIG. 6b).

The bone resection device of the invention includes a device for controlling the pivotal positions of the blades 106, 108 relative to the housing 104, similarly to the device shown in FIG. 1. The pivot control device takes the form of a sleeve which has a hollow bore in which the shaft 102 is received. At its distal end, the pivot control device has two parallel arms with aligned bores, and a pin 118 extends between the arms through bores. Axial movement of the sleeve relative to the shaft 102 causes the pin 118 to move axially relative to the housing 104.

Figure 7:
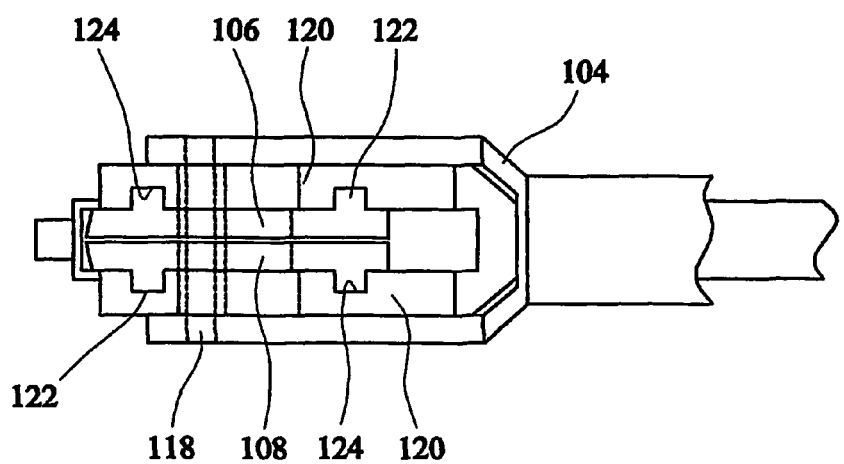
FIG. 7 is a side view of the resection device shown in FIGS. 6a and 6b, along an axis which is perpendicular to the axis for the side views in FIGS. 6a and 6b.

As shown in FIG. 7, each of the blades 106, 108 is held in the housing between two cheek plates 120 which are fixed in the housing. The blades can slide between the cheek plates, each of the blades having a rib 122 in its side wall, and each of the cheek plates having grooves 124 in which the ribs can slide. The rib and groove arrangement defines the sliding path for the blades relative to the housing. The sliding path can be straight, or non-straight, for example curved. Each of the blades has a slot 126, 128 in it which is arranged at an angle to the axis of the shaft 102. Movement of the pin 118 relative to the housing, within the slots 126, 128 in the blades causes the blades to be displaced along their respective sliding paths. FIG. 6a shows the blades at or towards their retracted position and FIG. 6b shows the blades at or towards their extended position.

The instrument of the invention will be made largely from metallic materials which are used commonly for surgical instruments. Certain stainless steels will generally be preferred.

The invention claimed is:

1. A bone resection device for use in resection of bone during joint replacement surgery, the device comprising:
    a handle;
    an elongate shaft rotatably mounted to the handle, the shaft having a shaft axis, a proximal end and a distal end;
    a cutting tool housing attached to the shaft at or towards the distal end of the shaft;
    at least one cutting tool fastened to the cutting tool housing, the at least one cutting tool configured to be movable between a retracted position and an extended position;
    a pivot control member having a proximal end and a distal end, the pivot control member configured to be at least partially disposed about the elongate shaft, the pivot control member being attached at or toward the distal end to the at least one cutting tool, the distal end of the pivot control member and the distal end of the shaft being configured to be axially displaceable with respect to one another a predetermined distance, during operation of the device; and
    a cam follower, and wherein one of the pivot control member and the shaft comprises a cam surface configured to accept the cam follower, the cam surface extending about the shaft axis in a plane generally perpendicular to the shaft axis, wherein one of the cam surface and the cam follower is fixed relative to the handle, and the other of the cam surface and the cam follower is fixed relative to the pivot control member, and wherein the cam surface is non-planar and varies axially from a first point to a second point radially offset from the first point.

2. The device of claim 1, wherein the at least one cutting tool comprises at least two cutting tools, each of which is at least partially disposed within the cutting tool housing when the at least two cutting tools are in their respective retracted positions.

3. The device of claim 2, wherein each of the at least two cutting tools is pivotally fastened to the cutting tool housing.

4. The device of claim 2, wherein the at least two cutting tools are configured to be fastened to the cutting tool housing in an opposed manner such that when one of the cutting tools is caused to move in one direction the other cutting tool is caused to move to about the same degree in the opposite direction.

5. The device of claim 1, wherein the distal end of the pivot control member is configured to be axially displaceable with respect to the distal end of the shaft a predetermined distance, during operation of the device.

6. The device of claim 5, further comprising a locking mechanism configured to lock the axial position of the shaft relative to the handle.

7. The device of claim 6, wherein the locking mechanism is configured to be adjustable to provide different locked axial positions of the shaft relative to the handle.

8. The device of claim 6, wherein the locking mechanism comprises a locking ring configured to fit on a portion of the shaft.

9. The device of claim 8, wherein the locking mechanism comprises a removable spacer ring configured to fit between the locking ring and the handle.

10. The device of claim 1, wherein the cam surface is provided on the proximal end of the pivot control member and the cam follower is fixed relative to the handle.

11. The device of claim 1, wherein the cam surface is provided on a removable part of the device.

12. The device of claim 1, wherein the shaft comprises a connector formation configured to be connected to a drive unit for imparting rotational movement to the shaft.

13. The device of claim 1, wherein the pivot control member is rotatable with the shaft relative to the handle.

14. The device of claim 13, wherein the pivot control member is connected to the shaft.

15. The device of claim 14, wherein the pivot control member is connected to the shaft at or towards the distal end of the shaft.

16. The device of claim 1, wherein one of the pivot control member and the at least one cutting tool has an elongate cam track formed therein and the other of the pivot control member and the at least one cutting tool comprises a follower configured to slide in the cam track.

17. The device of claim 16, wherein the cutting tool is generally elongate in shape, and has a cutting edge towards one end and one of the elongate cam track or follower at its other end.

18. The device of claim 16, wherein the cam track is non-parallel to the shaft axis.

19. The device of claim 1, wherein the at least one cutting tool has an elongate cam track formed therein and the pivot control member comprises a follower configured to slide in the cam track.

20. The device of claim 19, wherein the cutting tool housing has a slot and the follower is configured to extend through the slot and engage with the cam track of the at least one cutting tool.

21. The device of claim 20, further comprising a cam follower, and wherein the pivot control member is configured to move relative to the shaft, and one of the pivot control member and the shaft comprises a cam surface configured to accept the cam follower, the cam surface extending in a plane generally perpendicular to the shaft axis, and wherein one of the cam surface and the cam follower is fixed relative to the handle, and the other of the cam surface and the cam follower is fixed relative to the pivot control member.

22. The device of claim 1, wherein the predetermined distance is defined by a cam surface located on the proximal end of the pivot control member.

23. A bone resection device for use in resection of bone during joint replacement surgery, the device comprising:
    a handle;
    an elongate shaft rotatably mounted to the handle, the shaft having a shaft axis, a proximal end and a distal end;
    a cutting tool housing attached to the shaft at or towards the distal end of the shaft, the cutting tool housing having a slot;
    at least one cutting tool fastened to the cutting tool housing, the at least one cutting tool configured to be movable between a retracted position and an extended position, the at least one cutting tool having an elongate cam track formed therein; and
    a pivot control member having a proximal end and a distal end, the pivot control member comprising a follower extending generally perpendicular from the distal end thereof and configured to extend through the slot and engage with the cam track of the at least one cutting tool, the pivot control member configured to be at least partially disposed about the elongate shaft, the pivot control member being attached at or toward the distal end of the at least one cutting tool; and
    a cam follower, and wherein one of the pivot control member and the shaft comprises a cam surface configured to accept the cam follower, the cam surface extending about the shaft axis in a plane generally perpendicular to the shaft axis, wherein one of the cam surface and the cam follower is fixed relative to the handle, and the other of the cam surface and the cam follower is fixed relative to the pivot control member, and wherein the cam surface is non-planar and varies axially from a first point to a second point radially offset from the first point.

24. The device of claim 23, wherein the distal end of the pivot control member and the distal end of the shaft being configured to be axially displaceable with respect to one another a predetermined distance, during operation of the device.

\* \* \* \* \*